United States Patent [19]
Paraschac et al.

[11] Patent Number: 6,050,999
[45] Date of Patent: Apr. 18, 2000

[54] CORNEAL IMPLANT INTRODUCER AND METHOD OF USE

[75] Inventors: Joseph F. Paraschac, Santa Clara; John A. Scholl, Danville; Thomas A. Silvestrini, Alamo, all of Calif.

[73] Assignee: KeraVision, Inc., Fremont, Calif.

[21] Appl. No.: 08/993,594

[22] Filed: Dec. 18, 1997

[51] Int. Cl.$^7$ .................................................. A61F 9/00
[52] U.S. Cl. .................... 606/107; 606/1; 606/205; 623/4; 623/6; 604/62; 221/4; 219/636
[58] Field of Search ................ 606/107, 1, 205; 623/4, 6; 604/62; 221/4; 219/236

[56] References Cited

U.S. PATENT DOCUMENTS

| | | |
|---|---|---|
| 4,014,335 | 3/1977 | Arnold . |
| 4,086,914 | 5/1978 | Moore ............................................. 221/4 |
| 4,451,254 | 5/1984 | Dinius et al. ............................... 604/62 |
| 4,452,235 | 6/1984 | Reynolds . |
| 4,481,948 | 11/1984 | Sole ........................................ 219/236 |
| 4,573,998 | 3/1986 | Mazzocco . |
| 4,607,617 | 8/1986 | Choyce ...................................... 606/107 |
| 4,688,570 | 8/1987 | Kramer et al. . |
| 4,815,463 | 3/1989 | Hanna . |
| 4,834,094 | 5/1989 | Patton et al. . |
| 4,941,093 | 7/1990 | Marshall et al. . |
| 4,950,272 | 8/1990 | Smirmaul ................................. 606/107 |
| 5,090,955 | 2/1992 | Simon . |
| 5,098,443 | 3/1992 | Parel et al. . |
| 5,123,905 | 6/1992 | Kelman ..................................... 606/107 |
| 5,188,125 | 2/1993 | Kilmer et al. . |
| 5,190,552 | 3/1993 | Kelman ..................................... 606/107 |
| 5,242,373 | 9/1993 | Scott et al. . |
| 5,242,449 | 9/1993 | Zaleski ...................................... 606/107 |
| 5,300,118 | 4/1994 | Silvestrini et al. . |
| 5,318,047 | 6/1994 | Davenport et al. . |
| 5,354,333 | 10/1994 | Kammann et al. ............................. 623/6 |
| 5,372,580 | 12/1994 | Simon et al. . |
| 5,466,260 | 11/1995 | Silvestrini et al. . |
| 5,474,562 | 12/1995 | Orchowski et al. ..................... 606/107 |
| 5,505,722 | 4/1996 | Kilmer et al. . |
| 5,547,468 | 8/1996 | Simon et al. . |
| 5,607,437 | 3/1997 | Simon et al. . |
| 5,766,181 | 6/1998 | Chambers et al. ...................... 606/107 |
| 5,776,139 | 7/1998 | McDonald .............................. 606/107 |

FOREIGN PATENT DOCUMENTS

| | | |
|---|---|---|
| 0 392 773 | 10/1990 | European Pat. Off. . |
| 43 01 418 | 3/1995 | Germany . |
| WO 96/40005 | 12/1996 | WIPO . |
| WO 98/42409 | 10/1998 | WIPO . |

OTHER PUBLICATIONS

Dutch Ophthalmic Research Center publication of Standard Instruments: Microforceps (1997) 2 pages total.

Gonchar et al., "Interlayer refraction tunnel keratoplasty in correcting myopia and astigmatism" UDC 617.753.2+617.753.3–089:617.713–089.844 *Vestink Oftalm.* (1988) 104(4):25–30. (Russian to English translation).

*Primary Examiner*—Michael Buiz
*Assistant Examiner*—Tan-Uyen T. Ho
*Attorney, Agent, or Firm*—Morrison & Foerster LLP

[57] ABSTRACT

A device for introducing a corneal implant into a cornea of a human eye. The device includes a body, a member coupled thereto, and a guide portion. The body has a distal end and a proximal end. The guide portion is disposed at the distal end of the body and forms a channel. The guide portion is configured for laterally supporting the implant when positioned in the channel and the member is arranged to axially support the implant when positioned in the channel.

30 Claims, 12 Drawing Sheets

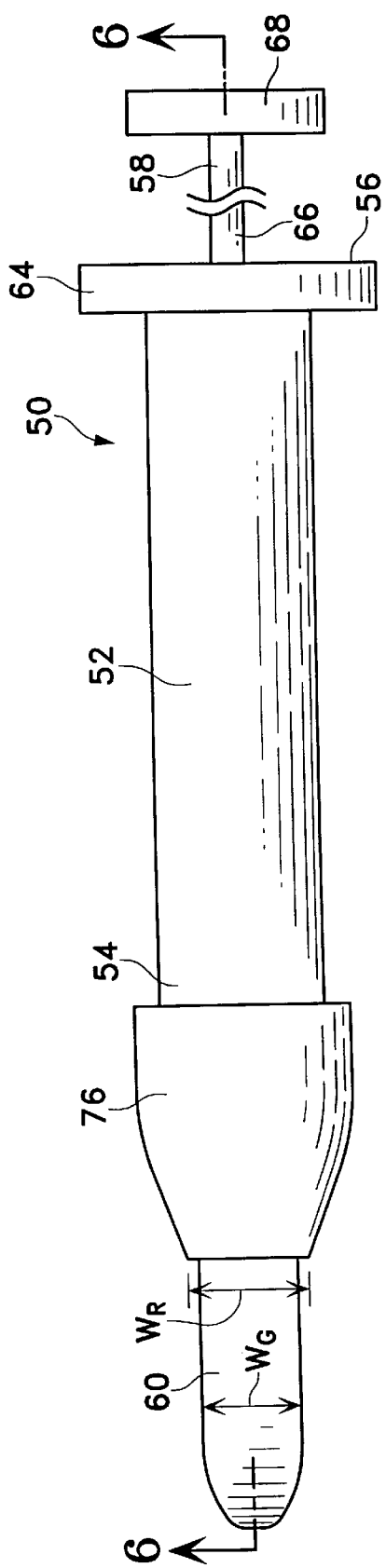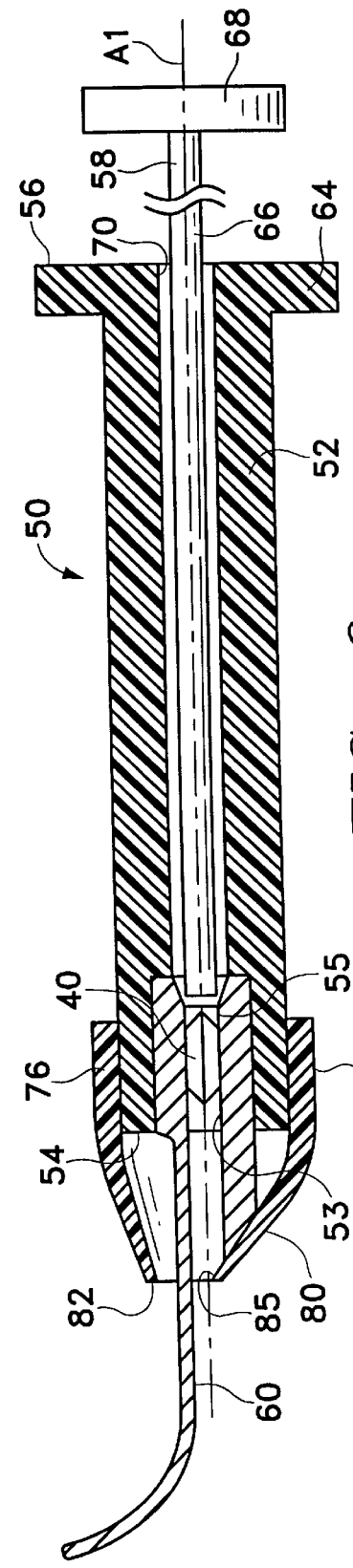
FIG. 5
FIG. 6

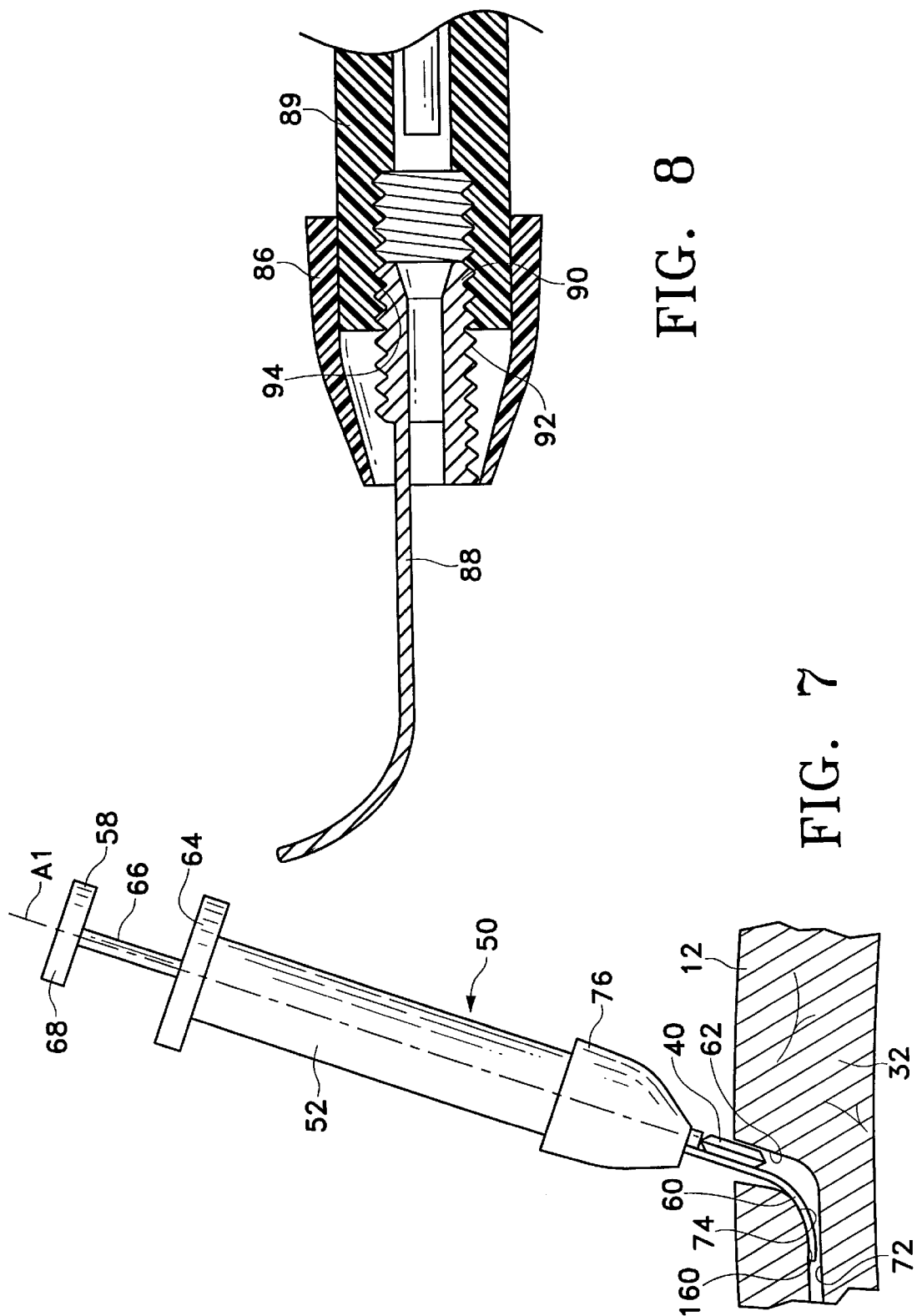

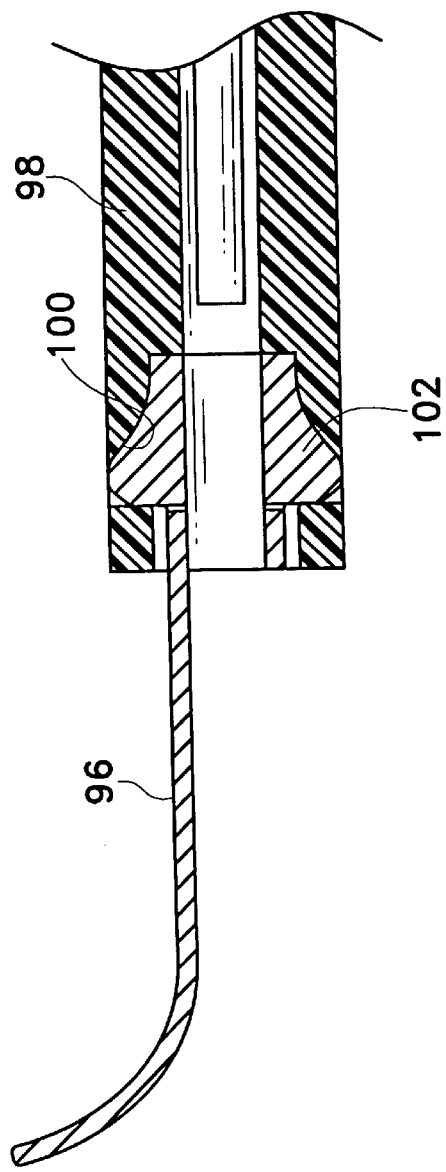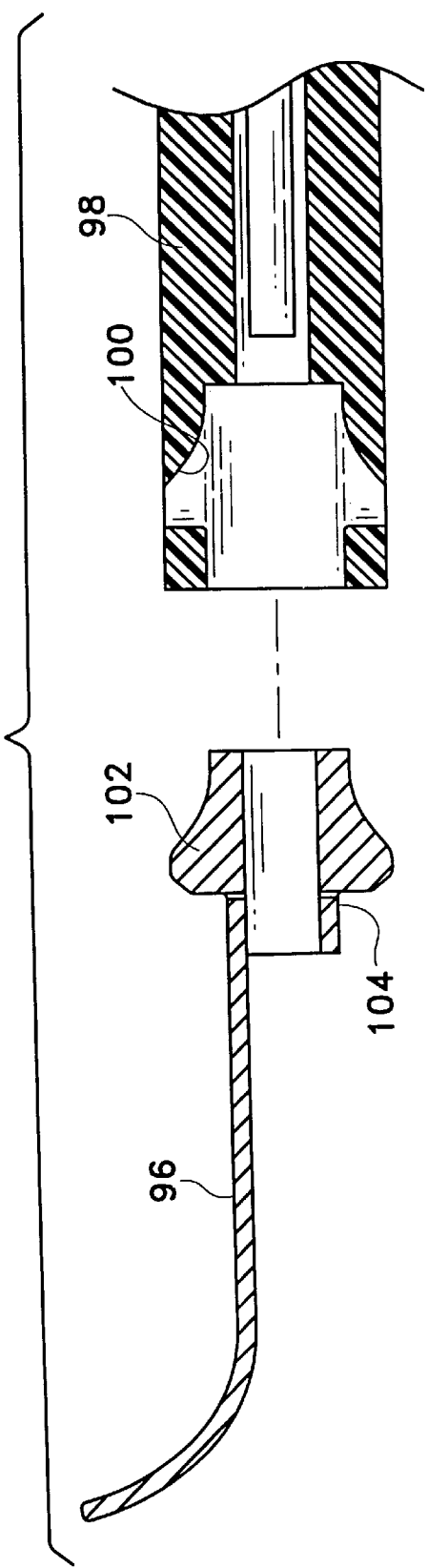
FIG. 9A
FIG. 9B

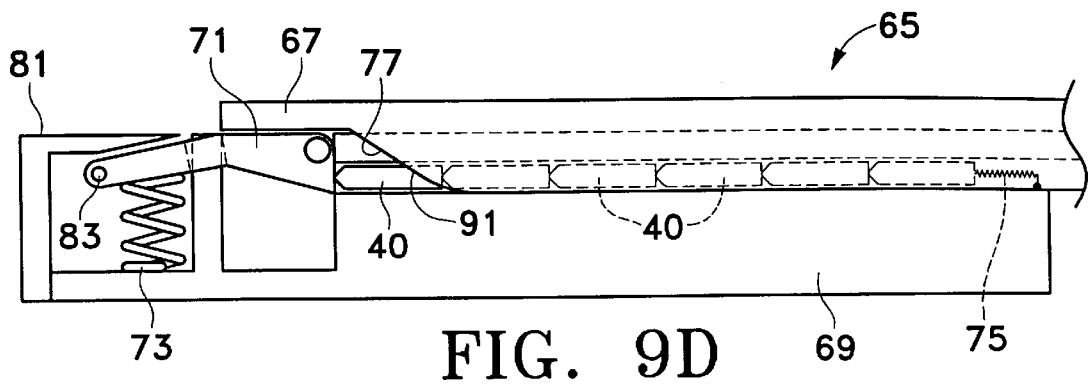
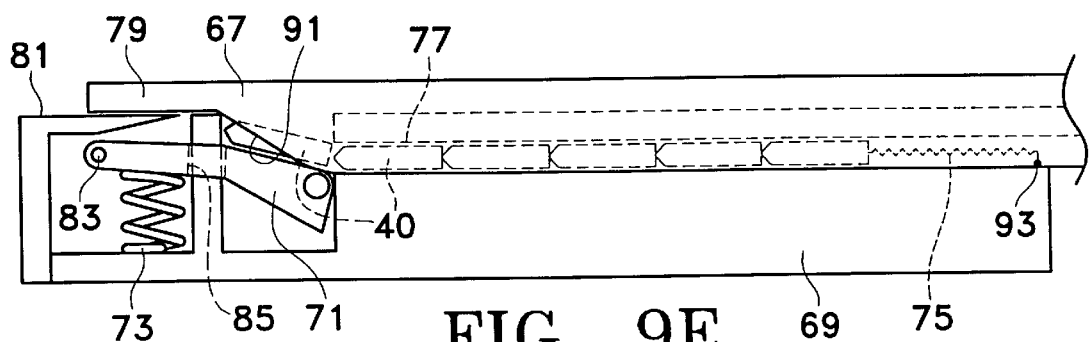
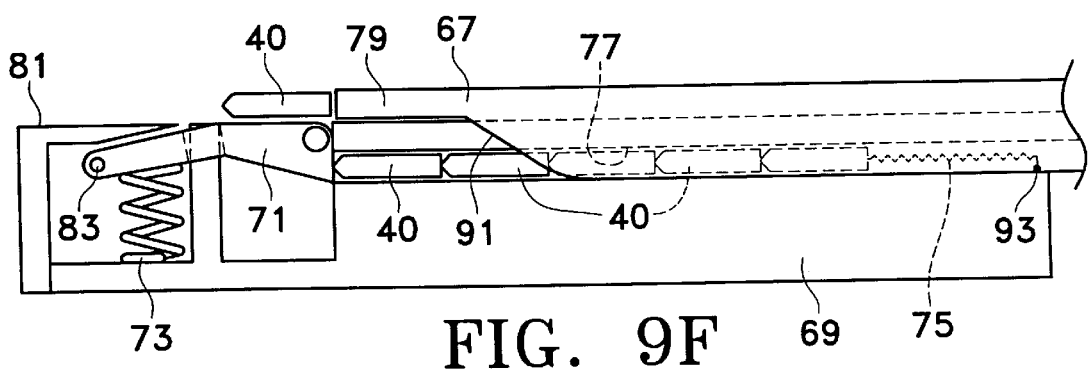
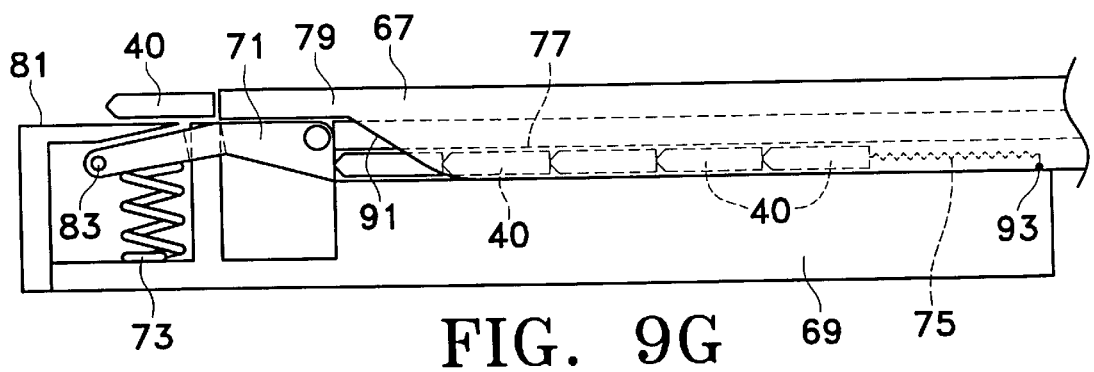

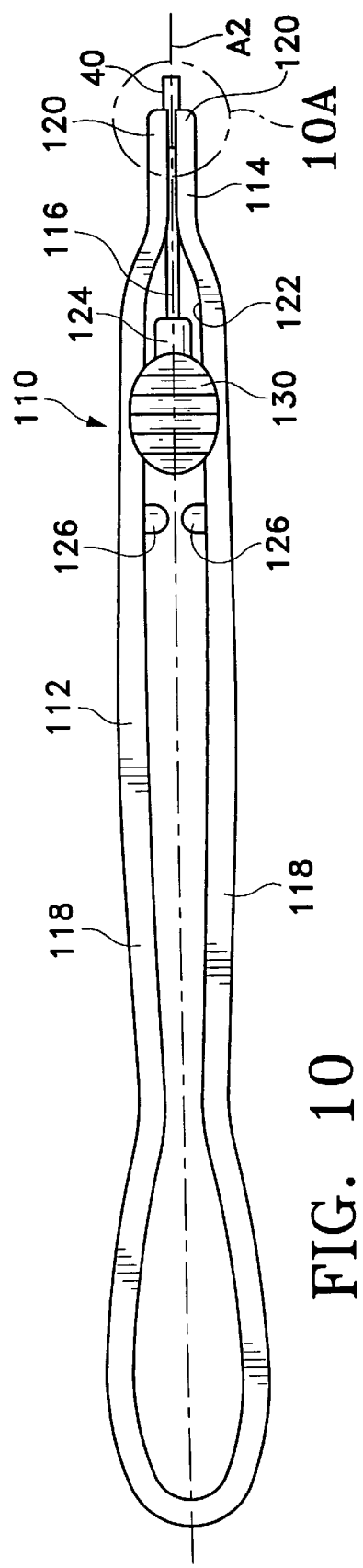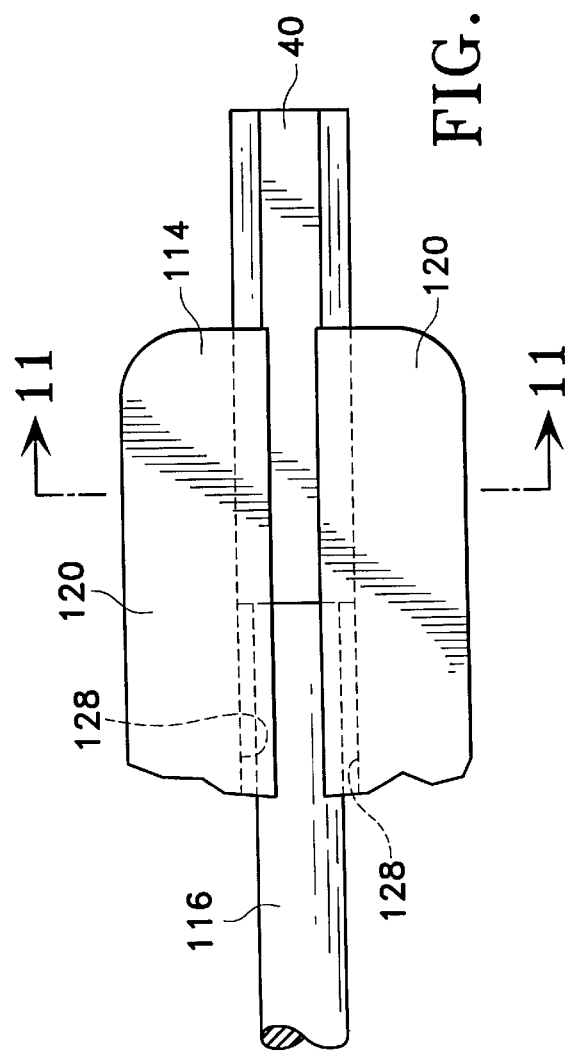
FIG. 10
FIG. 10A

CORNEAL IMPLANT INTRODUCER AND METHOD OF USE

BACKGROUND OF THE INVENTION

This invention relates generally to opthalmosurgical devices, and more particularly to a device used for the introduction of a corneal implant into the cornea of a mammalian eye. In general, such implants are used to adjust corneal curvature and correct vision abnormalities such as hyperopia.

Anomalies in the overall shape of the eye can cause visual disorders. Hyperopia ("farsightedness") occurs when the front-to-back distance in the eyeball is too short. In such a case, parallel rays originating greater than 20 feet from the eye focus behind the retina. Although minor amounts of hyperopia can be resolved in the human eye by a muscular action known as "accommodation", aging often compromises the ability of the eye to adequately accommodate. In contrast, when the front-to-back distance of the eyeball is too long, myopia ("nearsightedness") occurs and the focus of parallel rays entering the eye occurs in front of the retina. Astigmatism is a condition which occurs when the parallel rays of light do not focus to a single point within the eye, but rather have a variable focus due to the fact that the cornea refracts light in a different meridian at different distances. Some degree of astigmatism is normal, but where it is pronounced, the astigmatism must be corrected.

Hyperopia, myopia, and astigmatism are usually corrected by glasses or contact lenses. Surgical methods for the correction of such disorders are known. Such methods include radial keratotomy (see, e.g., U.S. Pat. Nos. 4,815,463 and 4,688,570) and laser corneal ablation (see, e.g., U.S. Pat. No. 4,941,093).

Another method for correcting these disorders is through the implantation of polymeric implants into the cornea instromal space to change the curvature of the cornea. Devices currently available for introducing the implants into the eye include standard forceps which are used to grasp the implant and manipulate it into an incision formed in the eye. The implant grasping surfaces of the forceps are typically flat or formed with small ridges, and do not conform to the specific shape of the implant. This makes it difficult to grasp the relatively small implants. Once the implant is picked up by the forceps, it is often difficult to retain the implant within the grasp of the forceps. If the implant is dropped it has to be sterilized again prior to use. These forceps are also not well suited for insertion of the implant into the incision. Because the forceps are designed to grasp the implant only along its sides to allow the forceps to release and regrasp the implant, the implant often backs out of the forceps during insertion into the eye. This also makes it difficult to push and manipulate the implant once it is partially inserted into the incision.

Furthermore, these forceps are configured for holding, and introducing into the eye only one implant at a time. This requires reloading and repositioning of the forceps prior to inserting each implant into the eye. Since the forceps are not designed for storage of the implants, the implants cannot be preloaded and packaged with the forceps.

SUMMARY OF THE INVENTION

The present invention involves an instrument which facilitates simple and accurate introduction of corneal implants (or inserts) into an eye to adjust corneal curvature and correct vision abnormalities. Among the features of the present invention may be noted the provision of a device which is designed to facilitate single-handed operation.

Generally, a device of this invention is for use in introducing a corneal implant into a cornea of a human eye. The device includes a body having a distal end and a proximal end, a guide portion disposed at the distal end and forming a channel, and a member coupled to the body. The guide portion is configured for laterally supporting the implant when positioned in the channel and the member is arranged to axially support the implant when positioned in the channel.

A method of the present invention includes the steps of providing a corneal implant in a holder and axially forcing the implant into an incision formed in the cornea of the eye.

The above is a brief description of some deficiencies in the prior art and advantages of the present invention. Other features, advantages, and embodiments of the invention will be apparent to those skilled in the art from the following description, accompanying drawings and claims.

BRIEF DESCRIPTION OF THE DRAWINGS

FIG. 5 is an elevational view of a device of the present invention for introducing the implant into an eye;

FIG. 6 is a cross-sectional view taken in the plane including line 6—6 of FIG. 5;

FIG. 7 shows the device of FIG. 5 introducing the implant into an eye;

FIG. 8 is a cross-sectional view of the device of FIG. 5 with a threaded connection between a slide and a body of the device;

FIG. 9A is a cross-sectional view of the device of FIG. 5 with a locked connection between the slide and the body of the device;

FIG. 9B is an exploded view of the device of FIG. 9A;

FIGS. 9D–9G are schematic illustrations of a cartridge for use with the device of FIG. 5;

FIG. 10 is a plan view of a second embodiment of a device of the present invention;

FIG. 10A is an enlarged fragmentary view of the device of FIG. 10;

Corresponding reference characters indicate corresponding parts throughout the several views of the drawings.

DESCRIPTION OF THE INVENTION

Prior to explaining the details of the inventive devices, a short explanation of the physiology of the eye is needed to appreciate the functional relationship of intracorneal implants or segments to the eye.

Figure 1:
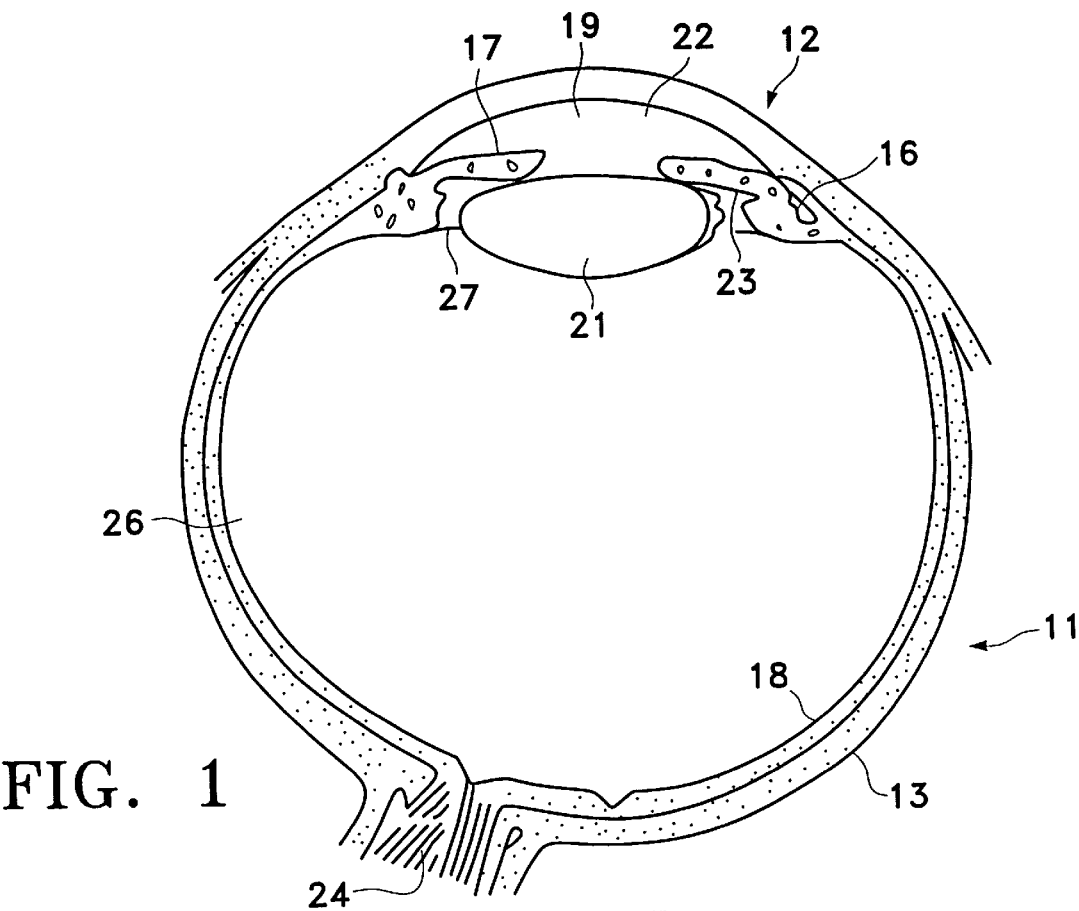
FIG. 1 is a schematic illustration of a horizontal section of an eye.

FIG. 1 shows a horizontal cross-section of the eye with the globe 11 of the eye resembling a sphere with an anterior bulged spherical portion representing the cornea 12. The globe 11 of the eye consists of three concentric coverings enclosing the various transparent media through which the light must pass before reaching the light-sensitive retina 18. The outermost covering is a fibrous protective portion the posterior, five-sixths of which is white and opaque and called the sclera 13, and sometimes referred to as the white of the eye where visible to the front. The anterior one-sixth of this outer layer is the transparent cornea 12.

A middle covering is mainly vascular and nutritive in function and is made up of the choroid, ciliary body 16, and iris 17. The choroid generally functions to maintain the retina 18. The ciliary body 16 is involved in suspending the lens 21 and accommodation of the lens. The iris 17 is the most anterior portion of the middle covering of the eye and is arranged in a frontal plane. It is a thin circular disc similar in function to the diaphragm of a camera, and is perforated near its center by a circular aperture called the pupil 19. The size of the pupil varies to regulate the amount of light which reaches the retina 18. It contracts also by accommodation, which serves to sharpen the focus by diminishing spherical aberration. The iris divides the space between the cornea 12 and the lens 21 into an anterior chamber 22 and the posterior chamber 23. The innermost portion of covering is the retina 18, consisting of nerve elements which form the true receptive portion for visual impressions.

The retina 18 is a part of the brain arising as an outgrowth from the fore-brain, with the optic nerve 24 serving as a fiber tract connecting the retina part of the brain with the fore-brain. A layer of rods and cones, lying just beneath a pigmented epithelium on the anterior wall of the retina serve as visual cells or photoreceptors which transform physical energy (light) into nerve impulses.

The vitreous body 26 is a transparent gelatinous mass which fills the posterior four-fifths of the globe 11. At its sides it supports the ciliary body 16 and the retina 18. A frontal saucer-shaped depression houses the lens.

The lens 21 of the eye is a transparent bi-convex body of crystalline appearance placed between the iris 17 and vitreous body 26. Its axial diameter varies markedly with accommodation. A ciliary zonule 27, consisting of transparent fibers passing between the ciliary body 16 and lens 21 serves to hold the lens 21 in position and enables the ciliary muscle to act on it.

Referring again to the cornea 12, this outermost fibrous transparent coating resembles a watch glass. Its curvature is somewhat greater than the rest of the globe and is ideally radially symmetric in nature. However, often it is more curved in one meridian than another giving rise to astigmatism. A central third of the cornea is called the optical zone with a slight flattening taking place outwardly thereof as the cornea thickens towards its periphery. Most of the refraction of the eye takes place through the cornea.

Figure 2:
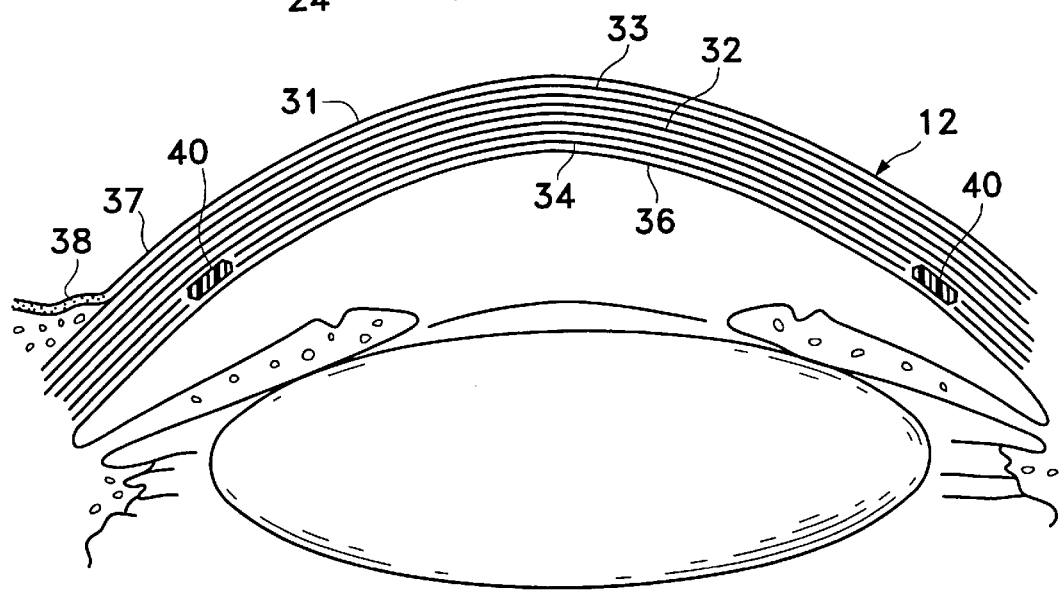
FIG. 2 is a schematic illustration of an anterior portion of the eye showing various layers of the cornea.

FIG. 2 is a more detailed drawing of the anterior portion of the globe showing the various layers of the cornea 12 making up the epithelium 31. Epithelial cells on the surface thereof function to maintain transparency of the cornea 12. These epithelial cells are rich in glycogen, enzymes and acetylcholine and their activity regulates the corneal corpuscles and controls the transport of water and electrolytes through the lamellae of the stroma 32 of the cornea 12.

An anterior limiting lamella 33, referred to as Bowman's membrane or layer, is positioned between the epithelium 31 and the stroma 32 of the cornea The corneal stroma 32 is made up of lamellae having bands of fibrils parallel to each other and crossing the whole of the cornea. While most of the fibrous bands are parallel to the surface, some are oblique, especially anteriorly. A posterior limiting lamella 34 is referred to as Descemet's membrane. It is a strong membrane sharply defined from the stroma 32 and resistant to pathological processes of the cornea. The endothelium 36 is the most posterior layer of the cornea and consists of a single layer of cells. The limbus 37 is the transition zone between the conjunctiva 38 and sclera on the one hand and the cornea 12 on the other.

Figure 3A:
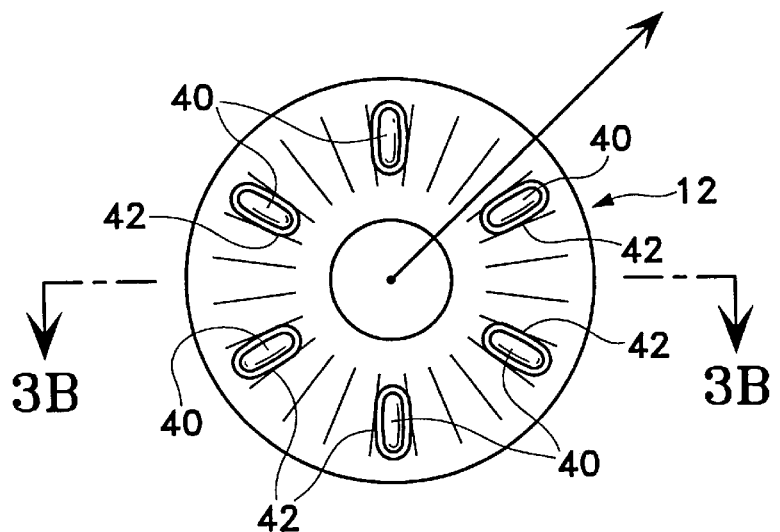
FIGS. 3A and 3B show respectively a front view and a cross-sectional view of a typical array of intracorneal implants inserted in an eye.
Figure 3B:
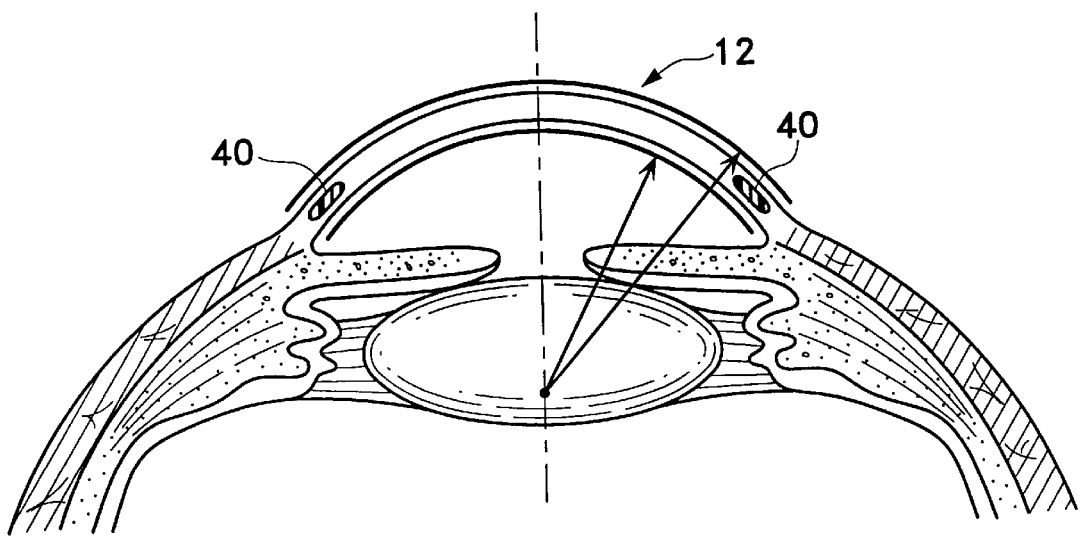

With that background in place, the present invention relates to the introduction of an implant 40 into the cornea 12, typically and desirably between the lamellar layers making up the cornea, in a position meridional to the cornea to alleviate abnormalities such as hyperopia. One or more of the implants 40 are typically inserted into the cornea 12 so that each subtends a portion of the meridian of the cornea outside of the cornea's central area, e.g., the area through which vision is achieved, but within the cornea's frontal diameter. FIGS. 3A and 3B show typical placement of the implants in the eye. FIG. 3A is a frontal view of the cornea 12 of an eye having six implants 40 which are located within small meridional pockets 42. A cross-sectional side view of the cornea 12 is shown in FIG. 3B.

Figure 4A:
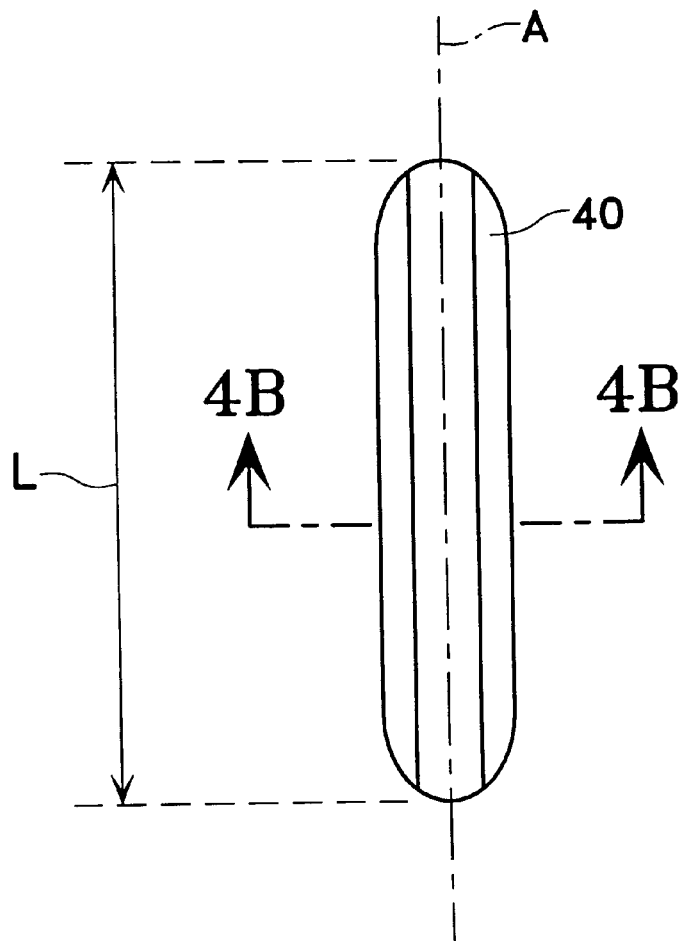
FIG. 4A is a plan view of a typical implant.
Figure 4B:
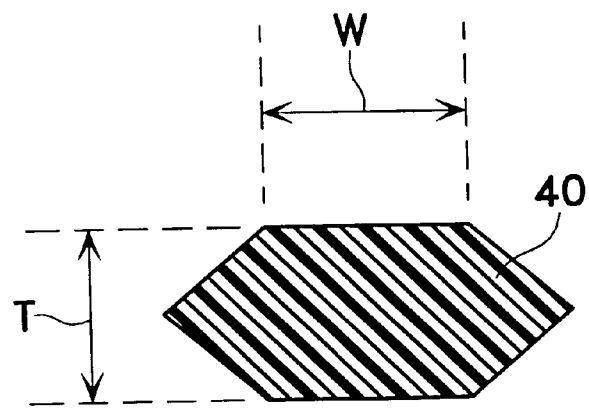
FIG. 4B is a cross-sectional view taken in the plane including line 4B—4B of FIG. 4A.

FIGS. 4A and 4B show one type of implant 40 which may be introduced into the eye by the devices of this invention. The implants 40 are preferably formed from a relatively stiff, physiologically acceptable polymer, but may be formed from other materials, or may be formed from a hybrid of different materials. The implant 40 has a central longitudinal axis A which may be arcuate or straight. As shown in FIG. 4B, the implant has a hexagonal shape as viewed in transverse cross section. The implant 40 may have a width W of between 0.2 mm and 2.0 mm, a thickness T of between 0.15 mm and 0.5 mm, and a length L less than 3.0 mm, for example. One or both of the ends of the implant 40 may also be tapered. A complete disclosure of the structure and use of the implants 40 may be found in U.S. patent application Ser. No. 08/101,438, entitled Segmented Preformed Intrastromal Corneal Insert, filed Aug. 2, 1993, Ser. No. 08/101,440, entitled Segmented Pliable Intrastromal Corneal Insert, filed Aug. 2, 1993, Ser. No. 08/485,400, entitled Radial Intrastromal Corneal Implant and a Method of Insertion, filed Jun. 7, 1995, and Ser. No. 08/662,781 entitled Radial Intrastromal Corneal Implant and a Method of Insertion, filed Jun. 7, 1996, (PCT No. PCT/US96/09768) and U.S. patent application entitled Radial Intrastromal Corneal Implant and a Method of Insertion, (continuation-in-part of Ser. No. 08/662,781), filed Dec. 18, 1997 (Attorney's Docket No. 25169-20028.20), the entirety of which are incorporated herein by reference. The above noted dimensions and shape are provided only as an example. It is to be understood that the shape and size of the implant 40, the location of the implant within the eye, or the number of implants, may be different than shown and described herein without departing from the scope of the invention.

Referring now to FIGS. 5 and 6, a device (or holder) of the present invention is generally indicated at 50. The device 50 comprises a body 52 having a distal end 54 and a proximal end 56, a guide portion 55 disposed at the distal end of the body and forming a channel 53, and a member coupled to the body. The guide portion 55 of the body 52 is configured for laterally supporting the implant when positioned in the channel 53 and the member is arranged to axially support the implant when positioned in the channel.

Figure 9C:
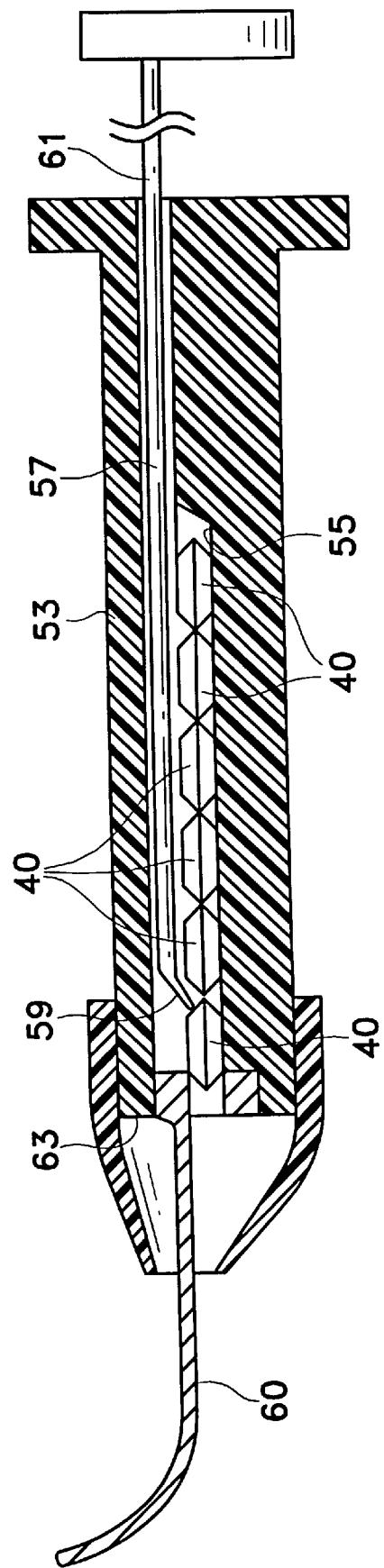
FIG. 9C is a cross-sectional view of the device of FIG. 5 modified to include an implant separator for introducing multiple implants.

The member comprises a drive member or piston 58 with the arrangement of the piston and implant 40 being such that as the piston moves in a distal direction (to the left as viewed in FIG. 6), the implant is urged along the channel 53 and into an incision formed in the corneal stroma, for introduction of the implant into the eye. A slide 60 extends from the distal end of the body 52 to guide the implant 40 and provide a surface against which the implant may slide to facilitate smooth insertion of the implant into the incision, as further described below. The implant is generally in its implanted configuration (FIG. 2, 3A, and 3B) when it is inserted into the device 50 and as it moves along channel 53, guide 55, and slide 60 of the device (FIGS. 6, 7, and 9C).

The body 52 is a generally tubular elongated member having an inside diameter slightly larger than the diameter of the piston 58 to allow for smooth axial movement of the piston. The proximal end 56 of the body 52 may include a peripheral rim 64 for engagement by a surgeon's fingers to assist in actuation of the piston 58. The body 52 may be formed from metal, a rigid polymer, or any other suitable material.

The piston 58 is in the form of a plunger similar in design to a plunger used in a syringe. The piston 58 comprises a rod 66, preferably having a length greater than the length of the body. A proximal end of the piston 58 has an enlarged portion 68 having a diameter greater than opening 70 in the proximal end 56 of the body 52 to limit the travel of the piston in the distal direction. The piston 58 is preferably sized such that when the enlarged portion 68 of the piston is in contact with the rim 64 of the body 52, the end of the piston rod 66 extends past the distal end 54 of the body so that the piston can push the entire implant 40 onto a surface of the slide 60. The piston 58 may be formed from metal, a stiff polymeric material or any other suitable material.

The slide 60 is located at the distal end 54 of the body 52 and is sized to fit within an incision 62 to guide the implant through the incision and into a pocket (or channel) 72 extending from the incision (FIG. 7). The slide 60 extends from a forward side of the body 52 and is preferably curved in a forward direction away from a central longitudinal axis $A_1$ of the device 50 so that the implant 40 is located rearward of the slide as it exits the body. This configuration allows the device 50 to guide the implant past a corner 74 defined by the intersection of the incision 62 and the pocket 72 (as further described below). The slide 60 is preferably formed from a rigid material to compress corner 74 to allow the implant 40 to move easily past the corner. The slide 60 may also be formed from a flexible material to allow the slide to bend around the corner 74. The width $W_G$ of the slide 60 is preferably greater than the width W of the implant 40, and the length of the slide is preferably greater than the depth of the incision (FIGS. 4B and 5). It is to be understood that the slide 60 may have configurations other than the one shown without departing from the scope of the invention. For example, the slide 60 may be straight for insertion into only the incision 62 rather than both the incision and the pocket 72. The slide 60 may be permanently attached to the body 52 by soldering, adhesives or any other suitable means. The slide 60 may also be removably connected to body 52 as described below.

The device 50 further includes a retaining member or ring 76 extending from the body 52 to the slide 60 to retain the implant 40 within the device prior to introducing the implant into the eye (FIG. 6). The ring 76 comprises a first portion 78 which is generally cylindrical in shape and sized to fit over the distal end 54 of the body 52, and a second portion 80 having a generally tapered surface extending from the first portion to a distal end 82 of the ring. The distal end 82 of the ring 76 has a width $W_R$ slightly larger than the width $W_G$ of the slide 60 so that the ring may extend over the slide. The ring 76 is formed from a resilient, expansible material which stretches to allow the implant 40 to pass through an opening 85 in the distal end 82 of the ring. As shown in FIG. 6, the opening 85 is sized so that the implant 40 must be pushed out from the ring 76 by the piston 58. As the piston 58 moves the implant 40 in the distal direction, the implant causes the opening 85 in the ring 76 to expand so that the insert can pass through. This design prevents the implant 40 from inadvertently falling out of the body 52 through the opening 85 in the ring 76. A ring 86 may also be sized to allow the implant 40 to pass freely therethrough without requiring the material of the ring to stretch (see FIG. 8). The ring 76, 86 is preferably formed from a smooth material which is compatible with the eye to prevent damage to the cornea 12 if the ring contacts the cornea. The ring 76, 86 may be configured for insertion into a portion of the incision 62, or may include a shoulder (not shown) for engagement with the cornea so that the device may rest on the cornea during introduction of the implant into the eye. The distal end of the ring 76, 86 may also be beveled to prevent inadvertent contact with the cornea. It is to be understood that other types of rings may be used, or the device may be used without a ring. For example, the retaining member may comprise a flap disposed on the distal end 54 of the body 52 to hold the implants in place within the device.

FIG. 8 shows a slide 88 which is threadably connected to a body 89 for easy removal and replacement of the slide. The slide 88 has a stem 90 extending from the end opposite the curved end of the slide. The stem 90 is hollow and generally cylindrical in shape. External threads 92 are formed on an outer surface of the stem 90. The body 89 has internal threads 94 formed thereon for mating with the external threads 92 on the stem 90 of the slide 88.

A locking connection between a slide 96 and a body 98 is shown in FIGS. 9A and 9B. The body 98 includes a first locking element 100 for engagement with a second locking element 102 formed on a stem 104 of the slide 96. The locking element 102 of the slide 96 snaps into the locking element 100 of the body 98. Other types of locking or interengageable components may be used to removably connect the slide 96 to the body 98.

FIG. 9C shows a modification of the body and piston of the device 50 of FIG. 5. The inner diameter of a body 53 of the device has a groove 55 formed therein for receiving the implants 40. A piston 57 includes an implant separator 59 at a distal end thereof for separating the implants 40 so that only one implant at a time is dispensed from the device. The implant separator 59 is integrally formed with the piston rod 61 and is bent downward from a distal end of the piston rod. The implant separator 59 engages one end of the implant 40 located at the distal end 63 of the body 53, and pushes the implant along the slide 60. The piston 57 is then pulled in the proximal direction until the implant separator 59 engages the proximal end of the next implant. The piston rod 61 may have markings on it to show how far to pull the piston 57 from the body 53 in order to engage the next implant 40. The piston 57 is preferably stiff and may be formed from a cold worked stainless steel, nitinol, or any other suitable material.

A cartridge for use with the device 50 (FIG. 5) is schematically shown in FIGS. 9D–9G, and generally indicated at 65. The cartridge 65 may be inserted into body 52 to replace the piston 57 of device 50. The cartridge comprises a piston 67 slidable along a support 69, a lever 71 pivotally mounted on the support, a lever spring 73 for biasing the lever to a closed position, and a feeder spring 75. The piston 67 has a longitudinal channel 77 formed on a bottom side thereof for storing the implants 40. A pusher 79 extends from an upper side of the piston 67 and is used to push the implants 40 onto a guide surface 81 which is aligned with the slide 60 (shown in FIG. 5). The piston 67 also includes a camming surface 91 for engagement with lever 71. The lever 71 is pivotally connected to the support 69 by a pivot pin 83, and has an opening 85 for receiving a portion of the support upon which the lever slides in a generally radial direction. The lever 71 is movable between a closed position (FIG. 9F) in which the implants 40 are retained within the channel 77, and an open position (FIG. 9E) in which an implant 40 may be moved from the channel onto an upper surface of the lever.

Operation of the cartridge 65 is as follows. The implants 40 are placed on the support 69 and the piston 67 is positioned over the implants with the implants disposed within the channel 77 formed on the bottom side of the piston (FIG. 9D). The lever 71 is in its normally closed position with the lever spring 73 forcing the lever against the piston 67. In order to move the lever 71 to its open position and release the first implant 40, the piston 67 is moved in a distal direction (to the left as viewed in FIG. 9E) and the camming surface 91 of the piston forces the lever downward into its open position. The piston 67 is then moved in a proximal direction to allow the lever 71 to move back to its closed position and push the implant 40 upward (FIG. 9F). The piston is next moved once again in the distal direction and the pusher 79 pushes the implant 40 onto the guide surface 81 and onto the slide 60 (FIGS. 6 and 9G). The implants 40 are constantly moved in the distal direction towards the lever by the feeder spring 75 which is connected to the support at 93. The cartridge 65 may also be used alone without the body 52 and slide 60 of device 50. The cartridge 65 may be loaded with the implants 40, and then sterilized and packaged, or the cartridge and implants may be inserted into the body 52 and sterilized and packaged as a complete device.

Figure 11:
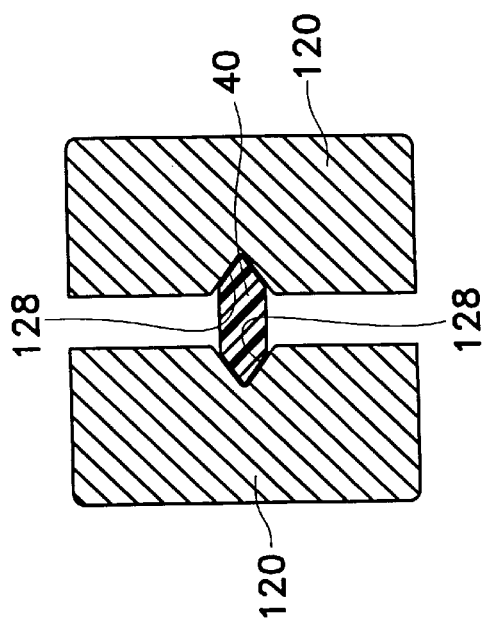
FIG. 11 is a cross-sectional view taken in the plane including line 11—11 of FIG. 10A.
Figure 12:
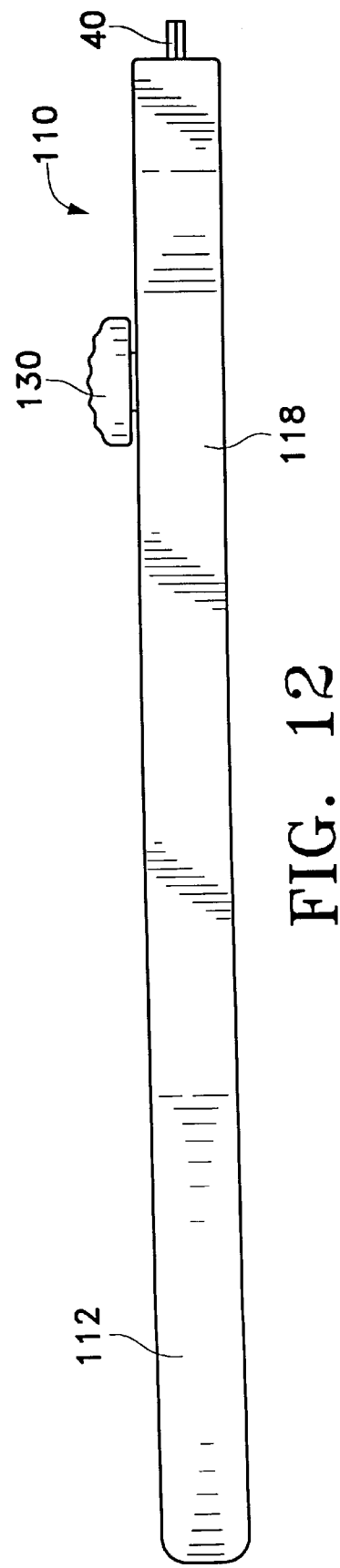
FIG. 12 is a side view of the device of FIG. 10.

A second embodiment of the present invention is generally indicated at 110 and shown in FIGS. 10–12. The device 110 comprises a body 112, a guide portion 114, and a piston 116 axially slidable in the body. The body 112 comprises a generally U-shaped member having two arms 118 extending generally parallel to a central longitudinal axis $A_2$ of the body, and forming a longitudinal slot 122 therebetween. End portions (or fingers) 120 of the arms 118 constitute the guide portion 114. The arms 118 are movably biased towards one another and are movable in a direction generally transverse to the longitudinal axis $A_2$ of the body 112. A cam 124 is connected to the piston 116 and is axially slidable along the slot 122 to urge the arms 118 outward and spread the fingers 120. Ramps 126 project from each arm into the slot 122 to provide camming surfaces for the cam 124. The cam 124 is located in a position distal to the ramps 126 when the fingers are in a closed position. As the cam 124 is moved in a proximal direction (to the left as viewed in FIG. 10) along the slot 122, the cam engages the ramps 126 and forces the arms 118 apart, thus causing the fingers 120 to move away from one another into an open position for loading the implants 40 into the device 110. As the cam 124 is moved in a distal direction, away from the ramps 126, the fingers 120 return to their closed position. The arms 118 may be bent so that the cam 124 engages the arms directly to open fingers 120, thus eliminating the ramps 126. The arms may also be formed as two separate pieces and attached to one another at their proximal ends.

Each finger 120 has a longitudinal groove 128 formed therein (FIG. 10A). The grooves 128 define a channel having a transverse cross-sectional shape corresponding to the transverse cross-sectional shape of the implant 40 (FIG. 11). The grooves 128 preferably have smooth surfaces to prevent damage to the implant as it moves through the channel. The piston 116 is operable to push the implant 40 along the channel and into the incision as the piston moves in a distal direction.

A pusher 130 is disposed above the cam 124 and arranged for actuation by a surgeon's thumb for simple one handed operation. The upper surface of the pusher 130 may be formed with ridges to increase the friction between the surgeon's thumb and the pusher for ease of operation. It is to be understood that configurations other than the one shown may be used without departing from the scope of the invention. For example, the piston 116 may be configured for actuation by a surgeon's index finger rather than the surgeon's thumb. The piston 116 may also be actuated by a rotary device (not shown) which causes axial movement of the piston to move the implant 40. A slide 60 similar to the one shown in the first embodiment 50, may also be attached to the ends of the fingers 120 to facilitate inserting and positioning the implants 40 in the incision 62 and pockets 72. The piston 116 and cam 124 may also be arranged to move in the same direction so that when the piston pushes the implant 40 towards the distal end of the fingers 120, the cam spreads the fingers apart.

Figure 13:
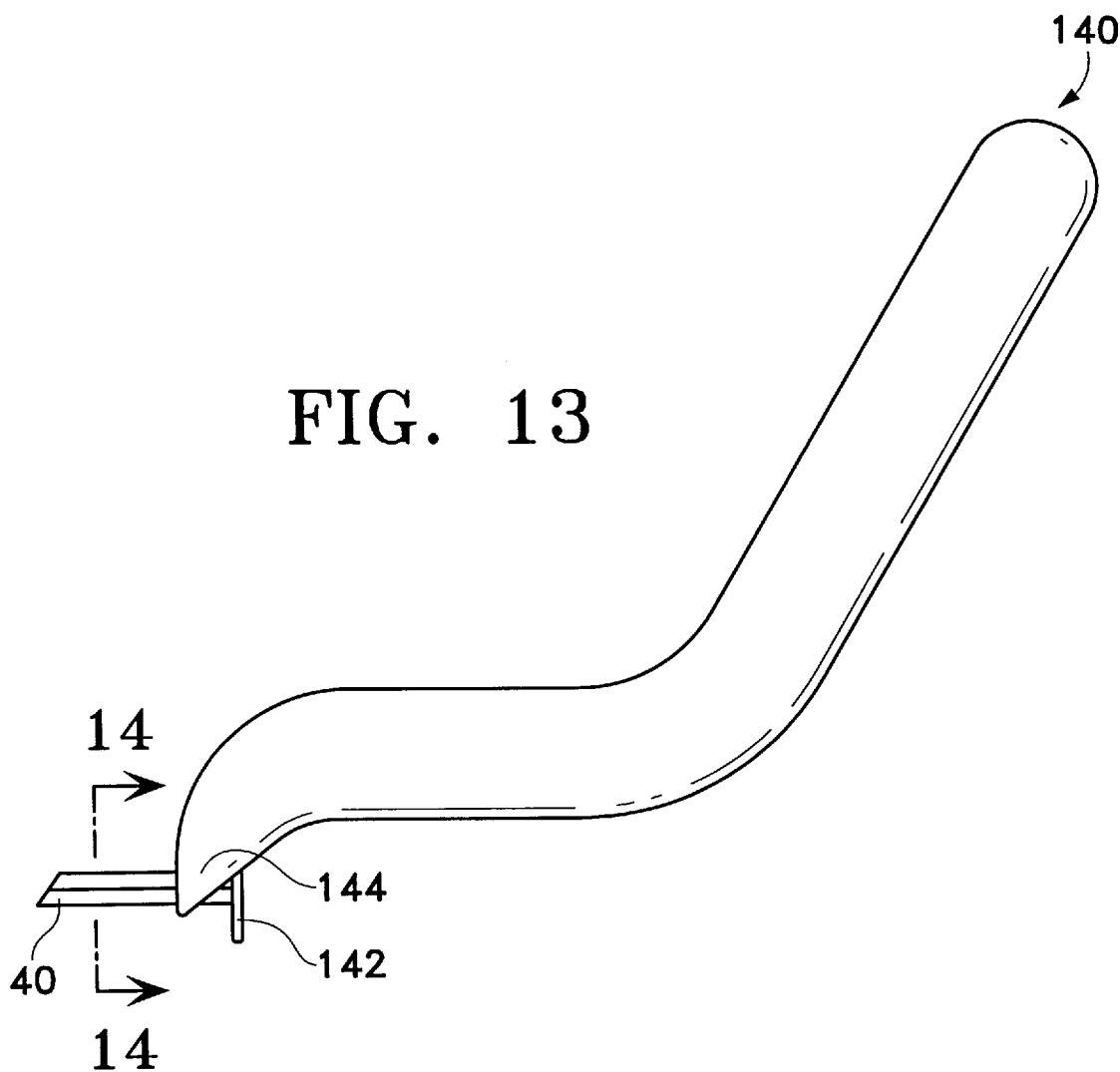
FIG. 13 is a side view of a third embodiment of a device of the present invention.
Figure 14:
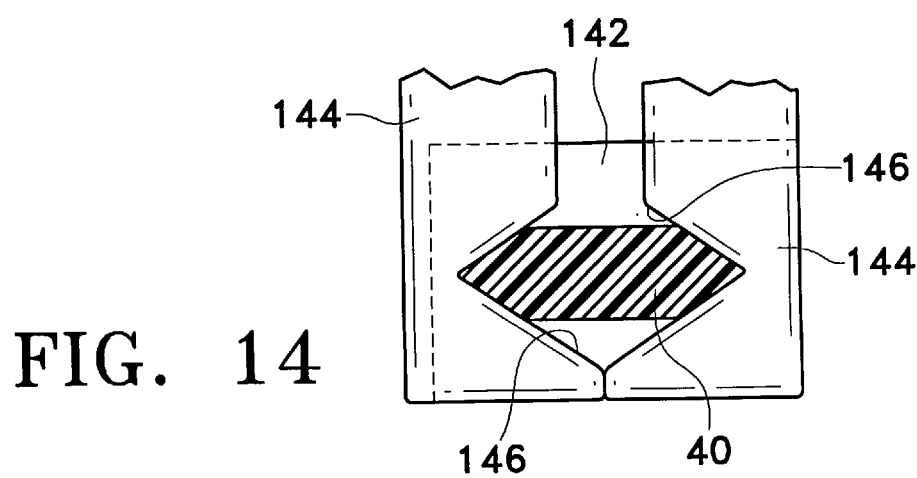
FIG. 14 is a cross-sectional fragmentary view taken in the plane including line 14—14 of FIG. 13.

A third embodiment of the present invention is shown in FIG. 13 and generally indicated at 140. The device 140 has two grasping fingers 144 (defining the guide portion), movable towards one another for holding the implant 40. The device has a stop (or flange) 142 to prevent the implant 40 from backing out from between the fingers 144. The fingers 144 preferably have grooves 146 formed therein to define a channel having a transverse cross-sectional shape generally corresponding to the transverse cross-sectional shape of the implant (FIG. 14). The stop 142 is attached to one side of one of the fingers 144 by welding, glue, or any other suitable method. The stop 142 may also be integrally formed with one of the fingers 144. In addition to limiting longitudinal movement of the implant 40 relative to the channel, the stop 142 is also used to apply a direct axial force to one end of the implant 40 to assist in pushing the implant into the incision 62 and manipulating the implant into its proper position.

The device 140 may also have hinge operated fingers (not shown) similar to forceps available from Dutch Ophthalmic Research Center International (D.O.R.C.) of Kingston, N.H., under trade designation MICROFORCEPS 1286C or 1286 DIA. The forceps include a sleeve which is axially movable in one direction to extend partially over the fingers and force the fingers into a closed position, and in the opposite direction to allow the fingers to spread apart. A flexible hinge is fixedly connected to the sleeve and actuated by movement in the radial direction to cause axial movement of the sleeve. The hinge is normally biased to a position in which the fingers are spread apart.

Figure 15:
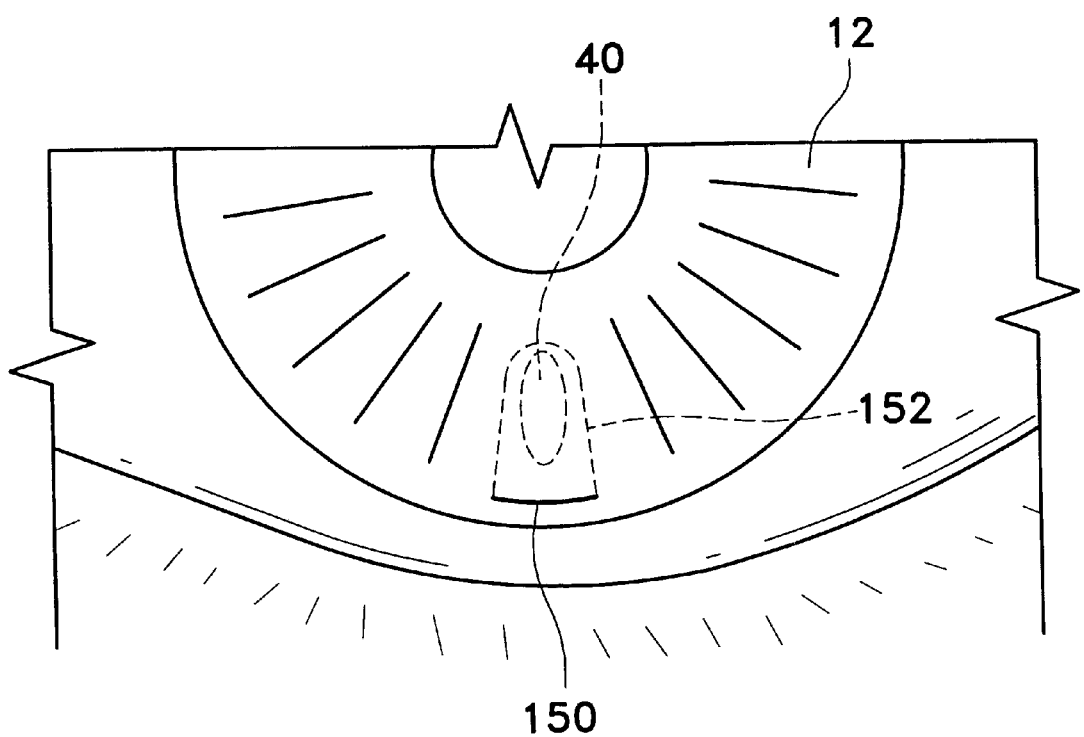
FIG. 15 is a schematic view showing the implant in an eye.

Procedures for creating an incision and a pocket, channel, or both in the cornea are disclosed in U.S. Pat. No. 5,300, 118, U.S. patent application Ser. No. 08/485,400, and U.S. patent applications entitled Radial Intrastromal Corneal Implant and a Method of Insertion, filed Dec. 18, 1997 (Attorney's Docket No. 25169-20028.20), and Corneal Pocketing Tool, filed Dec. 18, 1997 (Attorney's Docket No. 25169-20053.00), which are incorporated herein by reference. A small incision 62 is first made in the outer periphery of the anterior surface of the cornea 12. The implant 40 may be inserted into a single incision or through multiple incisions. For example, in the case of a single incision, a small meridional incision is made in the outer periphery of the anterior surface of the cornea. The incision may also be circumferential. FIG. 15 shows a small circumferential incision 150 and a meridional pocket 152 for placement of the implant. The incision 150 is shown located within the cornea 12, but the incision may also be made outside of the cornea 12, within the limbus of the eye. The pocket 152 is formed by inserting a blade of a pocket-forming device (not shown) through the incision 150 to separate stroma layers to form the pocket. The blade creates a stromal delamination for receiving the implant. The length, width and shape of the pocket are determined by the size and shape of the blade. The implant 40 is then introduced through the incision and into the pocket 152. A suitable positioning device may be used to properly position the implant 40 within the pocket. If required, the initial incision 150 may be closed by use of sutures, glue, staples, or by electrosurgical welding. It is to be understood that various other methods may be used to create the channels or pockets for the implants and other configurations or number of implants may be used without departing from the scope of the invention.

In order to use the device 50 of the first embodiment of this invention, one or more implants 40 are first loaded into the device (FIG. 6). The implant 40 is preferably loaded from the proximal end 56 of the body 52 by removing the piston 58 and placing the implants into the body lengthwise. The implant 40 may also be loaded into the distal end 54 of the body 52 through the ring 76. After the device 50 is loaded, it is placed near the incision 62 and the slide 60 is inserted into the incision (FIG. 7). The slide 60 is positioned adjacent to an upper edge 160 of the pocket 72. The piston 58 is slowly actuated to advance the implant 40 into the incision 62, rearward of the slide 60. The slide 60 prevents the implant 40 from getting caught on the corner 74 and allows for smooth insertion and positioning of the implant. After the implant 40 is properly inserted into the pocket 72, the slide 60 is removed from the incision 62. Multiple implants 40 may be inserted through the same incision 62.

The device 110 of the second embodiment is loaded axially from the open end of the fingers 120 (FIG. 10). The pusher 130 is moved in the proximal direction until the cam 124 engages the ramps 126 extending from the arms 118. The fingers 120 are now spread apart and the implant 40 may be loaded into the fingers. The pusher 130 is then moved in the distal direction to close the fingers 120 to grasp the implant 40. The device 110 is positioned over the incision and the pusher 130 is moved in the distal direction to introduce the implant 40 into the incision.

An implant 40 is inserted into the fingers 144 of the device 140 of the third embodiment in a method similar to the grasping of an implant with standard forceps, except that the implant is positioned with one end contiguous with the stop 142 (FIG. 13). The opposite end of the implant 40 is then inserted into the incision and the stop 142 prevents the implant from backing out from between the fingers 144. The stop 142 also helps to push the implant 40 into the incision and properly position the implant.

The devices may be sterilized using known procedures with sterilants such as ethylene oxide, radiation, or any other suitable sterilant. The devices are preferably packaged in a sterilized condition. The implants may be loaded into the devices and packaged with the device. The implants may also be loaded into a cartridge which may be inserted into the device. The device can then be reused by inserting a new cartridge. Depending upon the chosen materials for the implant, the packaging may by dry and include an inert gas or contain a sterile fluid such as saline solution.

It will be observed from the foregoing that the devices of the present invention have numerous advantages over the prior art. Importantly, the devices provide for simple and accurate placement of the implants into the corneal stroma of the eye. The design of the devices allows for single-handed operation by the surgeon and allows for the introduction of multiple implants into the eye at one time. Furthermore, since the device is designed to hold multiple implants, the implants may be loaded into the device and packaged with the device.

All references cited herein are incorporated by reference.

In view of the above, it will be seen that the several objects of the invention are achieved and other advantageous results attained.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A device for introducing a corneal implant into a cornea of a human eye in an implanted configuration, the device comprising a body, a member coupled thereto, a guide portion, said guide portion being sized for receiving the corneal implant in its said implanted configuration, said body having a distal end and a proximal end, the guide portion being disposed at the distal end of the body and forming a channel, the guide portion being configured for laterally supporting the implant when positioned in the channel and the member being arranged to axially support the implant when positioned in the channel, and a slide extending distally from the guide portion and adapted for insertion into the eye, the slide being configured to expose a portion of the implant when positioned on the slide.

2. A device as set forth in claim 1 wherein the member comprises a drive member movable in a distal direction to urge the implant through at least a portion of the channel.

3. A device as set forth in claim 1 wherein the body comprises an elongated tubular member configured for receiving at least one implant with a longitudinal axis of the implant extending generally parallel to a central longitudinal axis of the device.

4. A device as set forth in claim 3 wherein the drive member comprises a plunger axially slidable within the tubular member.

5. A device as set forth in claim 3 further comprising a retaining member extending from a distal end of the tubular member for retaining the implant within the device.

6. A device as set forth in claim 5 wherein the retaining member comprises a ring extending over the distal end of the tubular member.

7. A device as set forth in claim 6 wherein a distal end of the ring is tapered.

8. A device as set forth in claim 6 wherein the ring is made from a flexible, resilient material.

9. A device for introducing a corneal implant into a cornea of a human eye in an implanted configuration, the device comprising a body, a member coupled thereto, and a guide portion, said guide portion being sized for receiving the corneal implant in its said implanted configuration, said body having a distal end and a proximal end, the guide portion being disposed at the distal end of the body and forming a channel, the guide portion being configured for laterally supporting the implant when positioned in the channel and the member being arranged to axially support the implant when positioned in the channel, the distal end of the ring being normally biased to a closed position to prevent the implant from being inadvertently dispensed from the device, the distal end of the ring being expansible to an open position to allow the implant to pass through an opening in the distal end of the ring.

10. A device as set forth in claim 1 further comprising a slide extending from the distal end of the body and adapted for insertion into an incision formed in the cornea of the eye.

11. A device as set forth in claim 10 wherein the slide is curved in a forward direction away from a central longitudinal axis of the device, the slide being positioned on the body such that the implant is located rearward of the slide as it exits the body.

12. A device as set forth in claim 10 wherein the slide is threadably connected to the body for removal and replacement of the slide.

13. A device as set forth in claim 10 wherein the body comprises a first locking element and the slide comprises a second locking element engageable with the first locking element for securely connecting the slide to the body.

14. A device for introducing a corneal implant into a cornea of a human eye, the device comprising a body, a guide portion, and a cartridge for storing and retaining a plurality of implants, the cartridge comprising a piston and a lever, the lever being movable between a closed position for retaining the implants within the cartridge, and an open position for releasing one implant from the cartridge, said body having a distal end and a proximal end, the guide portion being disposed at the distal end of the body, the guide portion being configured for laterally supporting the implant and the piston being arranged to axially support the implant when positioned on the guide.

15. A device as set forth in claim 14 wherein the lever is biased to its closed position, the piston being operable upon movement in a distal direction to pivotally move the lever from its closed position to its open position.

16. A device for introducing a corneal implant into a cornea of a human eye, the device comprising a body, a member coupled thereto, and a guide portion, said body having a distal end and a proximal end, the guide portion being disposed at the distal end of the body and forming a channel, the guide portion being configured for laterally supporting the implant when positioned in the channel and comprising a pair of fingers configured for grasping the implant therebetween, the fingers being movable between an open position for loading and releasing the implant into and from the device, and a closed position for holding the implant, each finger having a longitudinal groove formed therein, the grooves defining the channel when the fingers are in the closed position, and the member being arranged to axially support the implant when positioned in the channel.

17. A device as set forth in claim 16 wherein the channel has a generally hexagonal cross-sectional shape.

18. A device as set forth in claim 16 wherein the member comprises a piston operable to move the implant through the channel as the piston moves in a distal direction.

19. A device for introducing a corneal implant into a cornea of a human eye in an implanted configuration, the device comprising a body, a member coupled thereto, and a guide portion, said guide portion being sized for receiving the corneal implant in its said implanted configuration, said body having a distal end and a proximal end, the guide portion being disposed at the distal end of the body and forming a channel, the guide portion being configured for laterally supporting the implant when positioned in the channel and the member being arranged to axially support the implant when positioned in the channel, the guide portion comprising a pair of fingers configured for grasping the implant therebetween, the fingers being movable between an open position for loading and releasing the implant into and from the device, and a closed position for holding the implant, the fingers defining the channel when in the closed position, the body comprising a pair of generally parallel arms, the fingers extending from the arms, and further comprising a cam longitudinally slidable between the arms and operable to spread the arms to move the fingers to their open position.

20. A device as set forth in claim 16 wherein the member comprises a stop connected to one of the fingers for limiting longitudinal movement of the implant relative to the channel and preventing movement of the implant in a distal direction away from the eye during introduction of the implant into the eye, the channel having a cross-sectional shape generally corresponding to the cross-sectional shape of the implant.

21. A device for introducing a corneal implant into the cornea of a human eye in an implanted configuration, the device comprising a body having a distal end and a proximal end, a guide portion disposed at the distal end of the body and forming a channel, a corneal implant laterally supported within the channel in its said implanted configuration, a member coupled to said body such that it can provide axial support to the implant, and a slide extending distally from the guide portion and adapted for insertion into the eye, the slide being configured to expose a portion of the implant when positioned on the slide.

22. A device as set forth in claim 21 wherein the member comprises a piston slidably coupled to the body.

23. A device as set forth in claim 21 wherein the member comprises a flange fixedly coupled to the body for providing the axial support to the implant.

24. A method for introducing a corneal implant into a cornea of a mammalian eye in an implanted configuration comprising the steps of:
   making an incision in the eye;
   providing a corneal implant in a holder in its said implanted configuration;
   placing the implant directly adjacent to the eye without inserting the holder into the eye;
   axially forcing the implant into an incision formed in the cornea of the eye while the corneal implant remains in its said implanted configuration and the holder remains adjacent to the eye without insertion of the holder into the eye.

25. A method as set forth in claim 24 further comprising creating a stromal delamination to receive the implant.

26. A method for introducing a corneal implant into a cornea of a mammalian eye comprising the steps of:
   providing a corneal implant in a holder;
   placing the implant in the holder and sterilizing the holder after placing the implant into the holder; and
   axially forcing the implant into an incision formed in the cornea of the eye.

27. A method as set forth in claim 26 wherein placing the implant into the holder comprises placing a plurality of implants into a cartridge and inserting the cartridge into the holder.

28. A method as set forth in claim 24 wherein the step of providing a corneal implant in a holder comprises moving a piston in a proximal direction to move fingers of the holder away from one another to load the implant into the holder.

29. A method as set forth in claim 24 wherein the step of axially forcing the implant into the incision comprises moving a piston of the holder to force the implant into the incision.

30. A device for introducing a corneal implant into a cornea of a human eye, the device comprising a body, a member coupled thereto, a guide portion, and a slide extending from the distal end of the body and adapted for insertion into an incision formed in the cornea of the eye, at least a portion of the slide being generally planar, said body having a distal end and a proximal end, the guide portion being disposed at the distal end of the body and forming a channel, the guide portion being configured for laterally supporting the implant when positioned in the channel and the member being arranged to axially support the implant when positioned in the channel.

* * * * *